US00PP08849P

United States Patent [19]

Caldwell

[11] Patent Number: Plant 8,849

[45] Date of Patent: Jul. 26, 1994

[54] SPATHIPHYLLUM PLANT "BOND A"

[76] Inventor: E. Bond Caldwell, 18444 Townsend House Rd., Dade City, Pasco County, Fla. 33525

[21] Appl. No.: 162,727

[22] Filed: Dec. 3, 1993

[51] Int. Cl.[5] ..... A01H 5/00

[52] U.S. Cl. ..... Plt./88.1

[58] Field of Search ..... Plt. 88.1

*Primary Examiner*—James R. Feyrer,
*Attorney, Agent, or Firm*—Henderson & Sturm

[57] ABSTRACT

A new variety of Spathiphyllum is provided. The plant has attractive dense foliage, exceptionally well branching, and very abundant flowers with a relatively dark spadix well contrasting with the spathe.

2 Drawing Sheets

SUMMARY OF THE INVENTION

This invention relates to a new and distinct Spathiphyllum cultivar which is outstanding because of its exceptional well branching characteristic, attractive dense foliage, very abundant flowers with pretty, dark spadix well contrasting with the spathe and primarily selected for those characteristics being so selected from a planting of Spathiphyllum being grown near Altha, Fla. in a cultivated area.

ORIGIN AND ASEXUAL REPRODUCTION

Asexual reproduction of this cultivar by tissue culture was directed by me, such reproduction establishing that the plant does in fact maintain the characteristics described, in successive generations.

It should be noted that the plant was initially selected where grown in or near Altha, Fla. and has since been reproduced by plant tissue culture in the vicinity of Altha, Fla. with the characteristics stated, found to be maintained through successive generations as before recited.

The cultivar may further be described as having a number of distinctive characteristics which are enumerated in the succeeding specific description but broadly stated as comprising a medium size Spathiphyllum cultivar, suitable for 8 to 12 inch pots, which is exceptionally well branching, has attractive dense foliage, very abundant flowers with relatively dark spadix well contrasting with the spathe, and a good response to GA treatment makes this cultivar suitable for commercial distribution as a flowering pot plant.

I have chosen to identify this new cultivar as Spathiphyllum 'Bond A'.

It is possible that other identification will be adopted in the trade, but the name selected will serve for the purposes hereof.

BRIEF DESCRIPTION OF THE PHOTOGRAPHS

The accompanying photographs show as nearly true as it is reasonably possible to make the same, in a color illustration of this character, typical specimens of the plant parts of the new variety. The plants of the new variety were approximately 12 months from cutting propagation.

In the photographs:

FIG. 1 discloses the new variety;

FIG. 2 illustrates the spathe and spadix of a mature flower;

FIG. 3 illustrates a top of a mature leaf; and

FIG. 4 illustrates the bottom of a mature leaf.

DETAILED DESCRIPTION

In order to more specifically identify the cultivar descriptive details are set forth hereinafter, along with related aspects of the plant which serve to distinguish the same, all colors being noted as compared with The Royal Horticultural Society Colour Chart. The measurements and colors were recorded from mature plants grown in 10-inch diameter pots in the vicinity of Altha, Fla. Three fully developed units of each organ type were measured from each plant. Leaves penultimate to leaves subtending flowers were selected for measurement.

Parentage:

*Seed parent.*—Spathiphyllum 'Wallisii'.

*Pollen parent.*—Spathiphyllum 'Petite'.

Propagation: Plant Tissue Culture started near Altha, Fla.

Plant descriptions:

*Plant height.*—Top of leaf canopy 45–60 cm from soil level. Top of flowers 65–80 cm from the soil surface.

*Petioles.*—30–39 cm. Long, smooth. Geniculum 3.5–4.5 cm long, green (143 C) or yellow-green (144 A, B). Lower half of the adaxial side green (143 C) or yellow-green (144 A, B); forms a sheath at the time of a new leaf or flower emergence. The remaining part of a petiole green (137 A-C) with some addition of yellow-green (146 A).

*Leaves.*—Elliptic, acuminate tip with aristate tendencies, acute base with obtuse tendencies. Margins entire, wavy. Leaf surface slightly puckered. Young leaves emerge from petiole sheath of previous leaf. At maturity they are 26–30 cm long by 9.0–11.5 cm wide; width to length ratio 0.3:1 to 0.4:1.

*Color.*—Young expanding leaf similar to green (137 A, B) adaxial and yellow-green (147 B) to green (137 C) abaxial. Polished. Mature leaf similar to yellow-green (147 A) adaxial and green (137 C) or yellow-green (147 B) abaxial. Slightly polished.

*Veins.*—Midrib and primary veins well defined and sunken.

Flower:

*Type.*—Spathe and spadix. Young spathe tightly rolled around spadix and extrudes from petiole sheath. The spathe is fully opened approximately when peduncle is fully elongated. In a newly opened flower, spadix and the edge of spathe are slightly oblique to peduncle (they lean forward). At maturity they form approximately a straight line with the peduncle. Spathe cupped, shape intermediate between elliptic and ovate. Base intermediate between obtuse and acute, asymmetric (5-9 mm difference between the sides). Tip acuminate with aristate tendencies. Spathe is 12-15 cm in length, 5.5-8.0 cm in width; width to length ratio 0.4:1 to 0.5:1. Flowers produce slight fragrance.

*Spathe color.*—White (155 A) before opening; at maturity white (similar to 155 C and D) both adaxial and abaxial. On the abaxial side: midrib yellow-green (144 B central and 144 A on the edges), narrowing and becoming less prominent near tip; primary veins have similar coloration. Spathe tip yellow-green (144 B) but adaxially less visible.

*Spathe veins.*—Slightly sunken, abaxially more conspicuous due to coloration described above.

*Peduncle.*—60 to 69.5 cm. Shortly after emerging from the petiole sheath it is yellow-green (144 A-B). At maturity one of a range of green (137 C, 143 A, B) may occur. Peduncles slightly lean from the vertical.

Reproduction organs:

*Spathe.*—4.7-7.0 cm long, 1.8-2.0 cm wide.

*Stamens.*—Some anthers become visible at the base of pistils shortly before releasing pollen. Filaments not clearly visible.

*Pistil.*—Attenuate, exserted well beyond perianth.

*Color.*—At maturity, perianth greyed-yellow (160 D) pistils greyed-yellow (160 B).

*Flowering time.*—Full Spring flowering (3-5 flowers in a 10 inch diameter pot) within 14 months.

*Roots.*—White fleshly main roots with yellow root caps. Branching infrequent, abundant root hairs.

*Diseases.*—No unusual susceptibility to diseases noted to date.

*Insects.*—No unusual susceptibility to insects noted to date.

*General observations.*—Spathiphyllum 'Bond A' is a medium size Spathiphyllum cultivar, suitable for 8- for 12-inch pots. It is exceptionally well branching, has attractive dense foliage, very abundant flowers with relatively dark spadix well contrasting with the spathe. It is very suitable for programmed production due to a good response to GA treatment.

The cultivar may be compared with known varieties along the following lines where observation were made on plants grown under similar conditions near Altha, Fla.

Spathiphyllum 'Starlight' ®

'Bond A' has shorter, more ovate, slightly lighter leaves.

'Bond A' branches more freely than 'Starlight' ®.

Spathiphyllum 'Petite'

'Bond A' has narrower leaves, and a darker spadix that better contrasts with the spathe. Pistils are more conspicuous. 'Bond A' branches more than 'Petite'.

Spathiphyllum 'Viscount Prima' TM

'Bond A' is smaller, branches more, has smaller and more linear-shaped leaves; smaller and more cupped spathes; greater contrast between spadix and spathe; and pistils are more conspicuous.

I claim:

1. A new and distinct cultivar of Spathiphyllum, substantially as described and illustrated herein, characterized particularly as to novelty by its exceptional well branching characteristic, attractive dense foliage, and very abundant flowers with relatively dark spadix well contrasting with the spathe, providing a cultivar well suited as a flowering pot plant having no unusual susceptibility to the traditional Spathiphyllum diseases and insects.

* * * * *

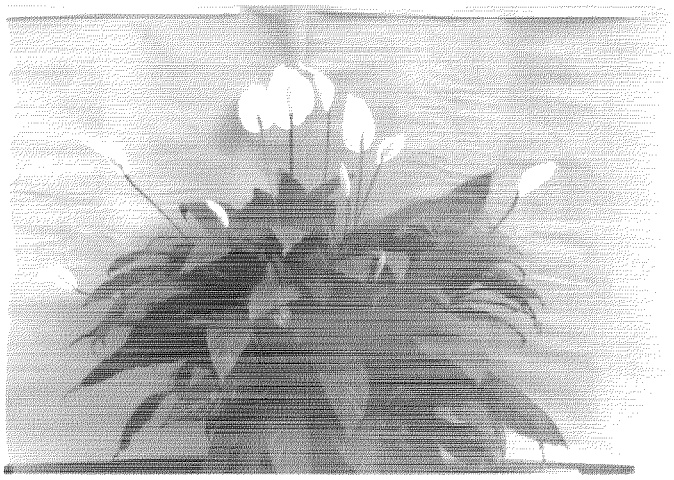
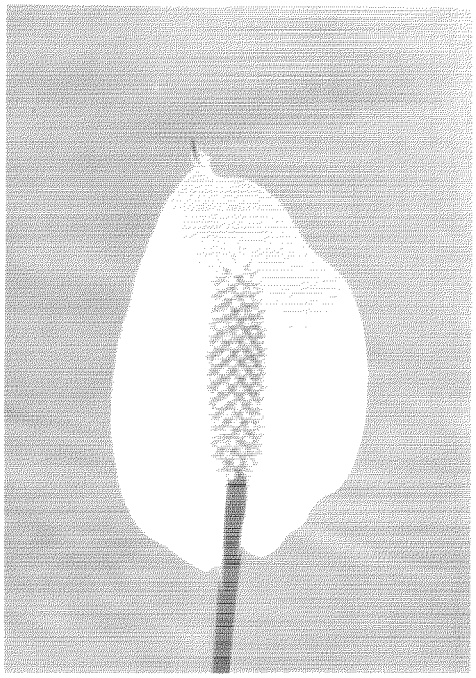

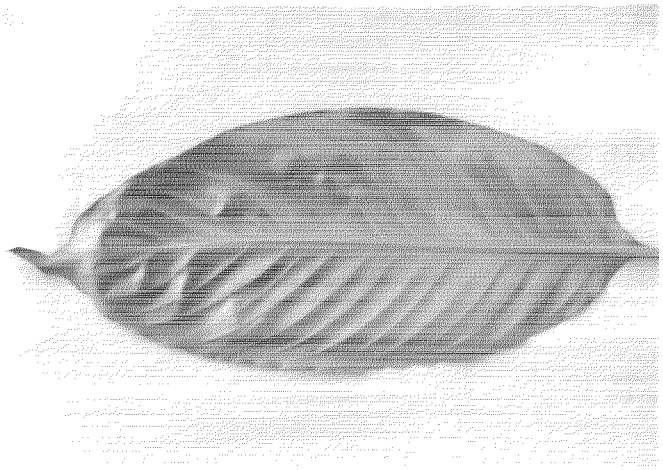
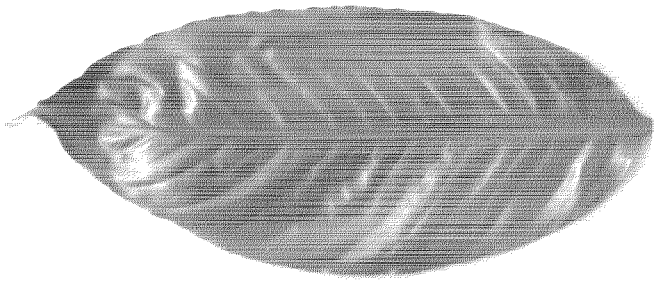

UNITED STATES PATENT AND TRADEMARK OFFICE

CERTIFICATE OF CORRECTION

PATENT NO. : PP8,849
DATED : July 26, 1994
INVENTOR(S) : E. Bond Caldwell

It is certified that error appears in the above-indentified patent and that said Letters Patent is hereby corrected as shown below:

Col. 3, line 32, the word "Reproduction" should be "Reproductive".

Col. 3, line 33, the word "Spathe" should be "Spadix".

Col. 3, line 43, the word "fleshly" should be "fleshy".

Signed and Sealed this

Fourteenth Day of March, 1995

Bruce Lehman

*Attest:*

BRUCE LEHMAN

*Attesting Officer*

*Commissioner of Patents and Trademarks*